(12) United States Patent
Braun

(10) Patent No.: US 6,224,856 B1
(45) Date of Patent: *May 1, 2001

(54) MEANS AND METHOD FOR TINTING KERATIN FIBERS, PARTICULARLY HUMAN HAIR

(75) Inventor: Hans-Juergen Braun, Ueberstorf (DE)

(73) Assignee: Wella Aktiengesellschaft, Darmstadt (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 12 days.

(21) Appl. No.: 09/091,090

(22) PCT Filed: Sep. 29, 1997

(86) PCT No.: PCT/EP97/05342

§ 371 Date: Jun. 11, 1998

§ 102(e) Date: Jun. 11, 1998

(87) PCT Pub. No.: WO98/17235

PCT Pub. Date: Apr. 30, 1998

(30) Foreign Application Priority Data

Oct. 18, 1996 (DE) .............................. 196 43 060

(51) Int. Cl.⁷ .................. A61K 7/06; A61K 7/13
(52) U.S. Cl. .................. 424/70.1; 424/401; 8/404; 8/405
(58) Field of Search .............. 8/404, 405; 424/70.6, 424/401, 70.1

(56) References Cited

U.S. PATENT DOCUMENTS

| | | | |
|---|---|---|---|
| 4,420,637 | * | 12/1983 | Bugaut et al. . |
| 5,207,798 | * | 5/1993 | Cotteret et al. . |
| 5,279,620 | * | 1/1994 | Junino et al. . |
| 5,540,738 | * | 7/1996 | Chan et al. . |
| 5,743,919 | * | 4/1998 | Moeller et al. . |
| 5,769,902 | * | 6/1998 | Semain . |

FOREIGN PATENT DOCUMENTS

| | | |
|---|---|---|
| 35 43 345 A1 | 6/1987 | (DE) . |
| 36 10 396 A1 | 10/1987 | (DE) . |
| 0 634 162 A1 | 1/1995 | (EP) . |
| 1063979 | * 4/1967 | (GB) . |

* cited by examiner

Primary Examiner—Thurman K. Page
Assistant Examiner—Brian K. Seidleck
(74) Attorney, Agent, or Firm—Michael J. Striker

(57) ABSTRACT

The dye precursor-containing composition for hair dyeing contains at least one p-aminophenol derivative compound of the formula (I):

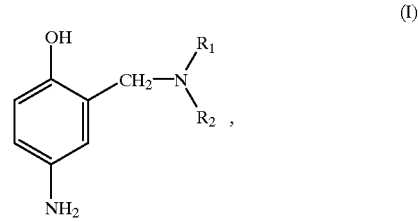

(I)

in which $R_1$ and $R_2$ each can be H, an alkyl, a hydroxyalkyl, an aminoalkyl, a mono- or dialkylaminoalkyl, an acylaminoalkyl, an aryl- or alkylsulfonylaminoalkyl, a carbamidoalkyl, an acyl, an aryl, an alkylsulfonyl or a carbomoyl group, each alkyl group having from 1 to 4 carbon atoms, or $R_1$ and $R_2$ together are part of a heterocyclic, non-aromatic 5- or 6-membered ring, with or without an oxo group; at least one 5-amino-2-methylphenol derivative compound of the formula (II),

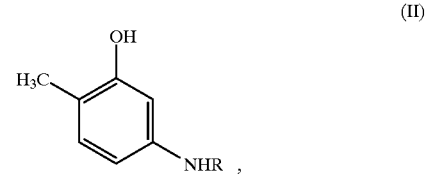

(II)

in which R is H, a $C_1$- to $C_4$-alkyl, a $C_2$- to $C_4$-hydroxyalkyl group or a $C_2$- to $C_4$- polyhydroxyalkyl group; and at least one m-phenylenediamine derivative compound of the formula (III),

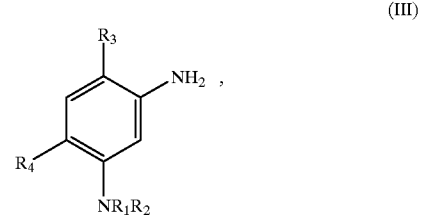

(III)

in which $R_1$ and $R_2$ each can be H, a $C_1$- to $C_4$-alkyl, a $C_2$- to $C_4$-hydroxyalkyl or a $C_3$- to $C_4$-polyhydroxyalkyl group; $R_3$ stands for H, a $C_1$- to $C_6$-alkyl, a $C_1$- to $C_4$-alkoxy, a $C_2$- to $C_4$-hydroxyalkyl or a $C_3$- to $C_4$-polyhydroxyalkyl group; and $R_4$ stands for H, a $C_1$- to $C_6$-alkyl, a $C_2$- to $C_4$-alkoxy, a $C_2$- to $C_4$-hydroxyalkyl or a $C_3$- to $C_4$-polyhydroxyalkyl group.

9 Claims, No Drawings

MEANS AND METHOD FOR TINTING KERATIN FIBERS, PARTICULARLY HUMAN HAIR

This application is a 371 of PCT/EP97/05342 filed Sep. 29, 1997.

BACKGROUND OF THE INVENTION

The present invention relates to a composition for dyeing keratinic fibers, especially human hair. These compositions contain at least one p-aminophenol, one m-aminophenol, and one m-phenylenediamine. The operations of dyeing the keratinic fibers are performed by mixing the aforementioned composition with an oxidant, applying it to the keratinic fibers, and after a certain action time washing it out again with water and a shampoo.

For a certain group of applications, there is a demand for compositions which are capable of dyeing the hair in copper-colored, chestnut-brown to red shades. This demand is currently being satisfied by putting hair dyes with a content of certain oxidative colorants on the market. For example, in German Published, Non-Examined Patent Application DE-OS 36 10 396, to produce neutral red tints, the use of a combination of 5-amino-2methylphenol, 4-amino-3-methylphenol and 1,4-diaminobenzene and/or 2,5-diaminotoluene is specified. In European Published Patent Application EP 0 634 162, examples are given for combining 5-amino-2-methylphenol and its n-substituted derivatives, 4-amino-2-methylphenol, 4-amino-3-methylphenol, 4-amino-2-hydroxymethylphenol, and certain m-phenylenediamine derivatives.

The resistance of the hair colorings produced by the prior art to the effects of light, washing, weathering, sweat, and other hair treatments is unsatisfactory, however.

SUMMARY OF THE INVENTION

It has now been surprisingly discovered that these disadvantages are avoided if a combination of the following dye precursors or dye compounds is used for oxidative hair coloring in the reddish color range:

at least one p-aminophenol derivative compounds in accordance with the general formula (I)

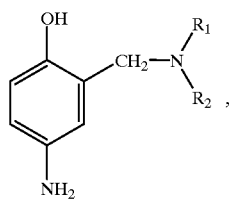

(I)

in which $R^1$ and $R^2$, independently of one another, stand for hydrogen, a straight-chained or branched alkyl radical, a straight-chained or branched hydroxyalkyl radical, a straight-chained or branched aminoalkyl radical, a straight-chained or branched mono- or dialkylaminoalkyl radical, a straight-chained or branched acylaminoalkyl radical, a straight-chained or branched aryl- or alkylsulfonylaminoalkyl radical, a straight-chained or branched carbamidoalkyl radical, a radical, an acyl radical, an aryl radical, a straight-chained or branched alkylsulfonyl radical, or a carbamoyl radical, in which the alkyl radical in each case has from 1 to 4 carbon atoms, or $R^1$ and $R^2$ form a heterocyclic, nonaromatic 5- or 6-side ring, which may additionally have an oxo group, or the salts of the aforementioned compounds;

at least one 5-amino-2-methylphenol derivative compound in accordance with the general formula (II),

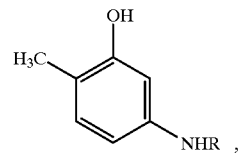

(II)

in which the radical R stands for hydrogen, a straight-chained or branched alkyl group having from 1 to 4 carbon atoms, a straight-chained or branched hydroxyalkyl group having from 2 to 4 carbon atoms, or a straight-chained or branched polyhydroxyalkyl group having from 3 to 4 carbon atoms;

at least one m-phenylenediamine derivative compounds in accordance with the general formula (III),

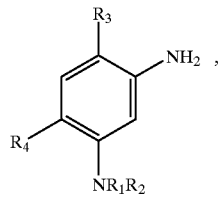

(III)

in which $R_1$ to $R_2$, independently of one another, stand for a hydrogen atom, a straight-chained or branched alkyl group having from 1 to 4 carbon atoms, a straight-chained or branched hydroxyalkyl group having from 2 to 4 carbon atoms, or a straight-chained or branched polyhydroxyalkyl group having from 3 to 4 carbon atoms; and wherein $R_3$ stands for a hydrogen atom, a straight-chained or branched alkyl group having from 1 to 6 carbon atoms, a straight-chained or branched alkoxy group having from 1 to 4 carbon atoms, a straight-chained or branched hydroxyalkyl group having from 2 to 4 carbon atoms, or a straight-chained or branched polyhydroxyalkyl group having from 3 to 4 carbon atoms; and $R_4$, independently of $R_1$, $R_2$ and $R_3$, stands for a hydrogen atom, a straight-chained or branched alkyl group having from 1 to 6 carbon atoms, a straight-chained or branched alkoxy group having from 1 to 4 carbon atoms, a straight-chained or branched hydroxyalkyl group having from 2 to 4 carbon atoms, or a straight-chained or branched polyhydroxyalkyl group having from 3 to 4 carbon atoms.

The synthesis and use of compounds in accordance with general formula (I) in oxidative hair dyes is known in principle from Published, Non-Examined German Patent Application DE-OS 35 43 345, but the combinations disclosed in the present application have surprising advantages with regard to stability in withstanding the damaging effect of light and air.

Preferred derivative compounds in accordance with general formula (I) are the compounds 4-amino-2-aminomethylphenol, 4-amino-2-[(2'-hydroxyethyl)aminomethyl]phenol and 4-amino-2-(dimethylaminomethyl)phenol.

Preferred derivative compounds in accordance with general formula (II) are the compounds 5-amino-2-methylphenol, 5-methylamino-2-methylphenol, and 5-[(2'-hydroxyethyl)amino]-2-methylphenol.

Preferred derivative compounds in accordance with general formula (II) are the compounds 2-amino-4-[(2'-hydroxyethyl)amino]anisole, and m-phenylenediamine.

In addition to the dye precursor compound combinations of at least one derivative compound according to formula (I), at least one derivative compound according to formula (II) and at least one derivative compound according to formula (III), the compositions according to the invention can also include a dye precursor compound combination of at least one derivative compound according to formula (I), at least one derivative compound according to formula (II) and at least one member selected from the group consisting of 2,4-diamino-1-(2'-hydroxyethoxy)benzene, 2,4-diamino-1-(2',3'-dihydroxypropoxy)benzene, 1,3-bis(2',4'-diaminophenoxy)propane and 1,5-bis(2'-hydroxyethoxy)-2,4-diaminobenzene.

To round out the outcome of dyeing and to create special dye effects, the hair dye may contain other oxidative colorant precursors, such as derivatives of p-phenylenediamine, for example 2-(2',5'-diaminophenyl)ethanol; resorcinol derivatives, such as resorcinol or 4-chlororesorcinol, amino and hydroxy derivatives of 1,3-benzodioxole, such as 5-hydroxy-1,3-benzodioxole or 5-((2'-hydroxyethylamino-1,3-benzodioxole; naphthalene derivatives, such as 1-hydroxynaphthalene, 1,5-dihydroxynaphthalene, or 1,7-dihydroxynaphthalene; and direct dyes, such as 2-amino-4,6-dinitrophenol, 2-ethylamino-4,6-dinitrophenol, 2-[(2'-hydroxyethyl)amino]-4,6-dinitrophenol, 2-amino-6-chloro-4-nitrophenol, or 2-chloro-6-ethylamino-4-nitrophenol.

The above-described combinations according to the invention of oxidative dye precursors and optionally direct dyes are applied for dyeing purposes in a suitable dye precursor-containing composition.

The subject of the present application therefore also relates to a ready-to-use composition for oxidatively dyeing hair which is prepared by mixing the dye precursor-containing composition of the invention with an oxidant immediately prior to use.

The dye precursor-containing composition according to the invention contains the above-described combinations according to the invention of oxidative hair colorants and optionally direct dyes either per so or in the form of biocompatible salts, for instance in the form of hydrochlorides, sulfates or tartrates, or in the case of phenols in the form of alkali phenolates.

The total concentration of color precursors or dye compounds is 0.1 to 10 weight %, preferably 0.2 to 6 weight %. The concentration of the individual hair colorings is 0.01 to 5 weight %, and preferably 0.1 to 4 weight %.

Typical cosmetic additives can also be contained in the dye precursor-containing composition, examples being such antioxidants as ascorbic acid, thioglycolic acid or sodium sulfite; perfume oils; complexing agents; wetting agents; emulsifiers; thickeners; conditioners, and others.

The form of preparation for the chromophore composition and also for the oxidative colorant for hair that is ready to use may for example be a solution, and in particular an aqueous or aqueous-alcohol solution. The particularly preferred forms of preparation, however, are a cream, gel, or emulsion. Their composition represents a mixture of the dye components with the additives typical for such preparations.

Conventional additives in solutions, creams, emulsions, or gels are for example solubilizers with water, low aliphatic alcohols, such as ethanol, n-propanol and isopropanol, or glycols, such as glycerin and 1,2-propylene glycol, and also neutralizers or emulsifiers selected from the anionic, cationic, amphoteric or non-ionic classes of surfactants, such as fatty alcohol sulfates, ethoxylated fatty alcohol sulfates, alkyl sulfonates, alkyl benzene sulfonates, alkyltrimethylammonium salts, alkyl betaines, ethoxylated fatty alcohols, ethoxylated nonylphenols, fatty acid alkanolamides, ethoxylated fatty alcohols, ethoxylated nonylphenols, fatty acid alkanolamides, ethoxylated fatty acid esters; also thickeners such as higher fatty alcohols, starch or cellulose derivatives; and vaseline, paraffin oil and fatty acids, as well as conditioners such as cationic resins, lanolin derivatives, cholesterol, pantothenic acid and betaine. The aforementioned ingredients are used in the customary quantities for such purposes, for example the neutralizers and emulsifiers in a concentration of approximately 0.5 to 30 weight % (referred to the chromophore composition), the thickeners in a quantity of approximately 0.1 to 25 weight % (referred to the chromophore composition) and the conditioners in a concentration of approximately 0.1 to 5.0 weight % (referred to the chromophore composition).

The ready-to-use hair dye composition in accordance with the invention is prepared immediately before use by mixing the chromophore composition with a liquid oxidant.

The dye precursor-containing composition and the oxidant in this case are mixed together in a weight ration of 5:1 to 1:3, with a weight ration of 1:1 to 1:2 being especially preferred.

In the mixing of the preferably alkaline dye precursor-containing composition, the pH-value of the ready-to-use hair dye according to the invention is adjusted by means of the usually acidic oxidant to a pH value that is varied by means of the quantities of alkali in the dye precursor-containing composition and of acid in the oxidant, and by the mixture ratio. The pH-value of the ready-to-use hair dye may be from 3 to 11, and preferably 5 to 9.

For adjusting the pH-value of the dye precursor-containing composition and the oxidant, one can use organic and inorganic acids such as phosphoric acid, ascorbic acid and lactic acid, or alkalis such as monoethanolamine, triethanolamine, 2-amino-2-methyl-1-propanol, ammonia, sodium hydroxide, potash lye, or tris(hydroxymethyl)aminomethane, depending on the desired pH-value.

For use in oxidative hair coloring, the above-described dye precursor-containing composition is mixed with an oxidant immediately before use, and an appropriate amount of the ready-to-use oxidative hair dye composition obtained that is suitable for the hair coloring treatment is applied to the hair, generally from about 60 to 200 grams, depending on the fullness of the hair.

As an oxidant, primarily hydrogen peroxide, or its addition compounds of uric acid, melamine, or sodium bromate, in the form of a 1 to 12%, and preferably a 6% aqueous solution, can be considered; hydrogen peroxide is preferred.

The ready-to-use composition in accordance with the invention is left to act on the hair for approximately 10 to 45 minutes at 15° to 50° C., preferably for 30 minutes; the hair is then rinsed with water and dried. If necessary, the hair may be washed with a shampoo after rinsing, and optionally may be re-rinsed with a weak organic acid, such as citric acid or tartaric acid. The hair is then dried.

The following examples are intended to explain the invention in further detail, without limiting it to these examples.

EXAMPLES

Example 1–6

Hair Dye Solutions with a Basic pH Value

The following dye solution is prepared:

| | |
|---|---|
| 10.0 g | Isopropanol |
| 10.0 g | Lauryl alcohol diglycol ether sulfate sodium salt (28% aqueous solution) |
| 10.0 g | Ammonia, 25% aqueous solution |
| 0.3 g | Ascorbic acid |
| X g | Color precursors per Table 1 |
| | Water, fully desalinated, in an amount to make |
| 100.0 g | |

For use, 10 g of hair dye solution are mixed with 10 g of hydrogen peroxide solution (6% solution in water). The oxidative hair dye obtained is applied in tiny strands of hair. After an action time of 30 minutes at 40° C., the hair is rinsed with water, shampooed, and dried.

TABLE 1

| Color precursors/Example | 1 | 2 | 3 | 4 | 5 | 6 |
|---|---|---|---|---|---|---|
| 4-Amino-2-aminomethylphenol dihydrochloride | 2.1 g | — | 2.1 g | — | 2.1 g | 4.0 g |
| 4-Amino-2-[(2-hydroxyethyl)aminophenol dihydrochloride | — | 2.6 g | — | 2.6 g | — | — |
| 5-Amino-2-methylphenol | 1.5 g | 1.5 g | 0.6 g | 0.6 g | — | 0.3 g |
| 5-[(2-Hydroxyethyl)-amino]-2-methylphenol | — | — | — | — | 0.8 g | 0.5 g |
| 2,4-Diamino-1-(2-hydroxyethoxy)-benzene dichloride | — | 0.3 g | 1.2 g | — | 1.2 g | 0.1 g |
| 1,3-Bis(2,4-diaminophenoxy)propane tetrahydrochloride | 0.5 g | — | — | — | — | 0.5 g |
| 2-Amino-4-[(2-hydroxyethyl)amino] anisole sulfate | 0.6 g | 0.6 g | — | — | — | 1.2 g |
| 1,5-Bis(2-hydroxyethoxy)-2,4-diaminobenzene hydrochloride | — | — | — | 1.5 g | — | — |

Color on bleached animal hair: 1) russet, 2) chestnut, 3) russet, 4) russet, 5) reddish-brown, 6) trendy reddish-brown
Color on 90%-gray hair: 1) palisander, 2) reddish-brown, 3) palisander, 4) palisander, 5) palisander, 6) reddish-brown

Example 7

Hair Dye in Cream Form

| | |
|---|---|
| 0.34 g | 2,5-Diaminophenylethyl alcohol sulfate |
| 1.31 g | 4-Amino-2-aminomethyphenol hydrochloride |
| 0.24 g | Resorcinol |
| 0.30 g | m-Aminophenol |
| 0.24 g | 2-Amino-4-(2'-hydroxyethyl) aminoanisole sulfate |
| 0.20 g | 5-Amino-2-methylphenol |
| 0.05 g | 2-Amino-6-chloro-4-nitrophenol |
| 0.10 g | 1-Naphthol |
| 15.00 g | Cetyl alcohol |
| 3.50 g | Sodium lauryl alcohol diglycol ether sulfate, 28% aqueous solution |
| 3.00 g | Ammonia, 25% aqueous solution |
| 0.30 g | Sodium sulfite, anhydrous |
| 75.42 g | Water |
| 100.00 g | |

10 g of this hair dye are mixed shortly before use with 10 ml of hydrogen peroxide solution (6% concentration). Then the mixture is applied to blonde virgin hair and left to act for 30 minutes at 40° C. After that, the hair is rinsed with water and dried. The hair has been dyed a palisander color.

Example 8

| | |
|---|---|
| 1.5 g | 5-Amino-2-methylphenol |
| 1.0 g | 4-Amino-2-aminomethylphenol hydrochloride |
| 0.6 g | 2,5-Diaminotoluene sulfate |
| 0.5 g | 2-Chloro-6-ethylamino-4-nitrophenol |
| 0.4 g | Sodium hydroxide, solid |
| 0.6 g | Ascorbic acid |
| 7.0 g | Isopropanol |
| 15.0 g | Oleic acid |
| 10.0 g | Ammonia, 25% aqueous solution |
| 62.5 g | Water |
| 100.0 g | |

Shortly before use, 50 g of this hair dye is mixed with 50 ml of hydrogen peroxide solution (6% concentration), and the mixture is left to act on blonde human hair for 30 minutes. After that, it is rinsed with water and then dried. An unusually intensive, glowing fiery red color is obtained.

Example 9

Hair Coloring Solution with Acid pH Value

| | |
|---|---|
| 0.30 g | 2-(2',5'-Diaminophenyl) ethanol sulfate |
| 0.18 g | 4-Chlororesorcinol |
| 0.30 g | -Amino-2-aminomethylphenol hydrochloride |
| 0.30 g | 1-Naphthol |
| 0.30 g | Ascorbic acid |
| 0.20 g | Sodium lauryl ether sulfate |
| 0.22 g | Ammonia, 25% aqueous solution |
| 98.12 g | Water |
| 100.00 g | |

The pH value of the chromophore composition is adjusted to a pH value of 6.8 with dilute phosphoric acid or a dilute ammonia solution.

Immediately before use, 20 g of the hair coloring solution are mixed with 20 g of a 6% aqueous hydrogen peroxide solution (pH=6.8), and the oxidative hair dye obtained (pH=6.8) is applied to bleached hair. After an action time of 30 minutes at room temperature, the hair is rinsed with water and dried.

The hair thus treated is colored a reddish-violet shade.

What is claimed is:

1. A dye-precursor-containing composition for dyeing hair comprising a dye precursor compound combination, wherein said dye precursor compound combination is selected from the group consisting of a combination 4-amino-2-aminomethylphenol, 5-amino-2methylphenol and 2,4-diamino-1-(2'-hydroxyethoxy)benzene, and a combination of 4-amino-2-aminomethylphenol, 5-amino-2-methyl-phenol and 2-amino-4-[(2'-hydroxyethyl)amino] anisole.

2. A dye-precursor-containing composition for dyeing hair as defined in claim 1 further comprising, in addition to said dye precursor compound combination, at least one oxidative dye precursor compound selected from the group consisting of p-phenylenediamine derivatives, resorcinol derivatives, derivatives of 1,3-benzodioxol having at least one amine group, derivatives of 1,3-benzodioxole having at least one hydroxy group and naphthalene derivatives.

3. A dye-precursor-containing composition for dyeing hair as defined in claim 1 further comprising, in addition to said dye precursor compound combination, at least one oxidative dye precursor compound selected from the group consisting of 2-(2',5'-diaminophenyl)ethanol, resorcinol, 4-chlororesorcinol, 5-hydroxy-1,3-benzodioxole, 5-(2-hydroxyethyl)amino-1,3-benzodioxole, 1-hydroxynaphthalene, 1,5-dihydroxynaphthalene and 1,7-dihydroxynaphthalene.

4. A dye-precursor-containing composition for dyeing hair as defined in claim 1 further comprising a cosmetic vehicle for said dye precursor compound combination.

5. A dye-precursor-containing composition as defined in claim 1, containing from 0.1 to 10 percent by weight of said dye precursor compound combination.

6. A dye-precursor-containing composition as defined in claim 1, further comprising cosmetic additive ingredients.

7. A method of producing a ready-to-apply composition for dyeing hair, said method comprising the steps of mixing a dye-precursor-containing composition for dyeing hair with an oxidant immediately prior to application of the ready-to-apply composition to the hair, wherein said dye-precursor-containing composition for dyeing hair comprises a dye precursor compound combination selected from the group consisting of a combination of 4-amino-2-aminomethylphenol, 5-amino-2-methylphenol and 2,4-diamino-1-(2'-hydroxyethoxy)-benzene, and a combination of 4-amino-2-aminomethylphenol, 5-amino-2-methylphenol and 2-amino-4-[(2'-hydroxyethyl)amino]anisole.

8. The method as defined in claim 7, wherein said dye-precursor-containing composition for dyeing hair is mixed with said oxidant in a weight ration of from 5:1 to 1:3.

9. A method for dyeing hair, said method comprising the steps of:
   a) providing a dye-precursor-containing composition for dyeing hair containing a dye precursor combination selected from the group consisting of a combination of 4-amino-2-aminomethylphenol, 5-amino-2-methylphenol and 2,4-diamino-1-(2'-hydroxyethoxy) benzene, and a combination of 4-amino-2aminomethylphenol, 5-amino-2-methylphenol and 2-amino-4-[(2'-hydroxyethyl)-amino]anisole;
   b) mixing said dye-precursor-containing composition for dyeing hair with an oxidant to obtain a ready-to-apply hair dye composition;
   c) applying the ready-to-apply hair dye composition to the hair according to the abundance of the hair;
   d) allowing the ready-to-apply hair dye composition to act on the hair for from 10 to 45 minutes at a temperature of from 15° to 50° C.; and
   e) subsequently rinsing the hair with water, shampooing and rinsing again as needed and then subsequently drying the hair.

\* \* \* \* \*